United States Patent
Erickson et al.

(10) Patent No.: US 8,950,578 B2
(45) Date of Patent: Feb. 10, 2015

(54) LANCET DISPENSER

(75) Inventors: Thomas E. Erickson, Crosslake, MN (US); James J. Erickson, Mound, MN (US)

(73) Assignee: Ultimed, Inc., Excelsior, MI (US)

( * ) Notice: Subject to any disclaimer, the term of this patent is extended or adjusted under 35 U.S.C. 154(b) by 1542 days.

(21) Appl. No.: 11/763,949

(22) Filed: Jun. 15, 2007

(65) Prior Publication Data

US 2008/0308441 A1   Dec. 18, 2008

(51) Int. Cl.
- *B65D 83/10* (2006.01)
- *A61B 19/02* (2006.01)
- *A61B 5/15* (2006.01)
- *A61M 5/32* (2006.01)
- *A61M 5/31* (2006.01)

(52) U.S. Cl.
CPC ........... *A61B 19/0288* (2013.01); *A61B 5/1411* (2013.01); *A61B 19/0262* (2013.01); *A61B 2019/0209* (2013.01); *A61B 2019/021* (2013.01); *A61M 5/3202* (2013.01); *A61M 5/3204* (2013.01); *A61M 5/3205* (2013.01); *A61M 2005/312* (2013.01)
USPC .............................. 206/364; 206/365; 206/370

(58) Field of Classification Search
USPC ......... 206/364–366, 370, 380, 602, 604, 606, 206/571, 483, 521; 210/410; 220/908
See application file for complete search history.

(56) References Cited

U.S. PATENT DOCUMENTS

| | | | |
|---|---|---|---|
| 4,230,118 A * | 10/1980 | Holman et al. ................ | 606/182 |
| 4,452,243 A * | 6/1984 | Leopoldi et al. .............. | 606/182 |
| 4,577,630 A * | 3/1986 | Nitzsche et al. .............. | 606/182 |
| 4,715,374 A | 12/1987 | Maggio | |
| 4,869,366 A * | 9/1989 | Bruno .......................... | 206/370 |
| 4,874,103 A * | 10/1989 | Quisenberry et al. ..... | 220/254.3 |
| 4,995,871 A * | 2/1991 | Sasaki et al. .................. | 604/110 |
| 5,152,775 A * | 10/1992 | Ruppert ........................ | 606/182 |
| 5,269,800 A * | 12/1993 | Davis, Jr. ...................... | 606/182 |
| 5,282,822 A | 2/1994 | Macors et al. | |
| 5,322,164 A * | 6/1994 | Richardson et al. .......... | 206/366 |
| 5,339,993 A * | 8/1994 | Groya et al. ............. | 222/153.02 |
| 5,415,312 A * | 5/1995 | Mueller ..................... | 220/254.3 |
| 5,791,471 A | 8/1998 | Radmand | |
| 6,042,595 A * | 3/2000 | Morita ........................... | 606/181 |
| 6,089,397 A * | 7/2000 | Van Melle ..................... | 220/270 |
| D437,223 S * | 2/2001 | Coy et al. ....................... | D9/447 |
| 6,247,592 B1 * | 6/2001 | Racicot et al. ................ | 206/366 |
| 6,612,456 B1 * | 9/2003 | Hundley et al. ............ | 220/254.3 |
| 6,783,537 B1 | 8/2004 | Kuhr et al. | |
| 2003/0106820 A1 * | 6/2003 | Kirchhofer ................... | 206/365 |
| 2003/0132129 A1 * | 7/2003 | Erickson ....................... | 206/366 |
| 2005/0027211 A1 | 2/2005 | Kuhr et al. | |
| 2005/0216046 A1 | 9/2005 | Yeoh et al. | |
| 2006/0278545 A1 | 12/2006 | Henning | |
| 2007/0119740 A1 * | 5/2007 | Clegg et al. ................... | 206/366 |

FOREIGN PATENT DOCUMENTS

WO   2007/065110 A2   6/2007

* cited by examiner

*Primary Examiner* — Anthony Stashick
*Assistant Examiner* — Kaushikkumar Desai
(74) *Attorney, Agent, or Firm* — Seager, Tufte & Wickhem LLC

(57) ABSTRACT

Medical dispensers having cap removal feature are disclosed. An illustrative medical dispenser can include a container body having an interior chamber adapted to contain a number of unused medical instruments, and an opening mechanism on the container body for providing access to the contents within the interior chamber. A gripping element on the exterior of the container body can be used to facilitate the removal of a portion of the medical instrument.

22 Claims, 14 Drawing Sheets

LANCET DISPENSER

FIELD

The present invention relates generally to the field of dispensers for medical devices. More specifically, the present invention pertains to dispensers for lancets, sharps, or other medical instruments.

BACKGROUND

Lancing devices or "lancets" are commonly used in a variety of medical applications for obtaining blood samples from a patient. In diabetic applications, for example, such devices are frequently used to obtain a blood sample for measuring an individual's blood glucose levels to ensure that they are within a permissible range. Other medical blood diagnostics frequently require the collection of a blood sample from an individual to be examined. Typically, such devices may be used obtain a relatively small blood sample on the order of only a few micro-liters by pushing a sharp lancet through the individual's skin such as into the finger pad or earlobe. The lancets typically have a needle tip coupled to a handle or base that can be gripped by the user or inserted into a lancing device for piercing the skin. A removable cap is often provided over the needle tip to prevent the individual from accidentally sticking themselves with the tip prior to use, and to facilitate the sterile storage of the lancets within the packaging.

The packaging for lancets is typically accomplished in loose form, with several lancets disposed in a disordered arrangement within a cardboard box or within a tube. In some cases, the lancets may each be individually stored within a blister pack or other sterilized packaging medium. For each lancing process, the user manually removes a lancet from the packaging and grips the base of the lancet. The protective cap provided over the needle tip is then removed by the user, exposing the needle tip for use. Once a blood sample has been obtained, the lancet can then be sealed again by inserting the protective cap back over the needle tip. The used lancet can then be disposed within a waste container.

The process of retrieving a new lancet from the packaging and removing the protective cap to expose the needle tip can be difficult for some individuals due to the relatively small size of the lancet and since the individual's dexterity may be lowered due to their medical condition. For diabetics, for example, the individual's hypoglycemic state may make the process of removing the protective cap more difficult or even prohibitive. The difficulty associated with dispensement and cap removal may, in some circumstances, encourage the individual to reuse the lancet several times, which is unacceptable for hygienic reasons. Moreover, since the lancets are often designed to be used only once and become rapidly blunt, such reuse of the lancet may lead to increasing pain and discomfort by the user.

BRIEF SUMMARY

The present invention pertains to medical dispensers for lancets, sharps, or other medical instruments. An illustrative medical dispenser can include a container body having a top, a bottom, and a number of sidewalls defining an interior chamber adapted to contain a number of medical instruments. An opening mechanism on the container body can be actuated between a first position and a second position for opening or closing an opening on the container body, allowing the user to gain access to the contents within the interior chamber.

A gripping element formed on the exterior of the container body can be configured to receive a portion of a medical instrument to prepare the instrument for use. In some embodiments, for example, the gripping element can include an indentation formed on the top of the container body configured in size and shape to receive a portion of the protective cap on an inserted lancet. The protective cap can be removed from the lancet, for example, by inserting the cap into the indentation and then pivoting the lid into place adjacent to the protective cap. Holding the cap securely in place within the indentation via the lid, the user can then rotate the handle grip of the lancet relative to the container body to remove the protective cap from the handle grip.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
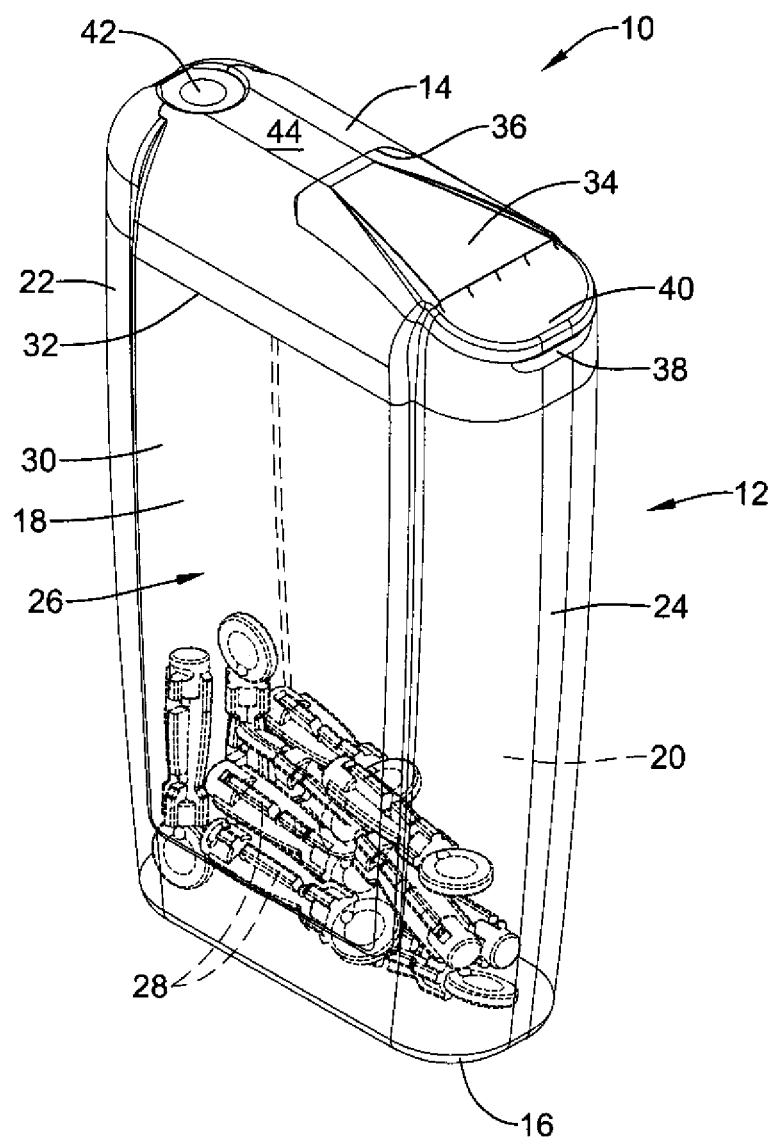
FIG. 1 is a perspective view showing an illustrative medical dispenser in accordance with an illustrative embodiment.

Referring now to FIG. 1, a perspective view of a medical dispenser 10 in accordance with an illustrative embodiment will now be described. As shown in FIG. 1, the dispenser 10 may include a container body 12 having a top 14, a bottom 16, and a number of sidewalls 18,20,22,24, which together define a container structure having an interior chamber 26 adapted to contain a number of unused lancets, sharps, or other medical instruments therein. As shown in phantom, for example, the interior chamber 26 may contain a number of unused lancets 28 that can be used by diabetic individuals for testing their blood sugar/glucose levels. In the illustrative embodiment depicted, the dispenser 10 may have a substantially rectangular shape with sidewalls 22 and 24 having a curved or rounded shape to facilitate gripping of the container body 12 by the user's hands. It should be understood, however, that the container body 12 may have any number of differently shaped configurations other than that depicted in FIG. 1.

The dispenser 10 can be configured to function as either a disposable dispenser or a reusable dispenser. In the latter case, for example, a seam 32 separating the top 14 from a lower portion 30 of the container body 12 may permit the top 14 to be temporarily removed, allowing the user to refill the interior chamber 26 with unused lancets 28 or other medical instruments, as desired. Alternatively, and in other embodiments, the top 14 can be fixedly secured to the lower portion 30 of the container body 12 to prevent the top 14 from being removed by the user. In one embodiment, for example, the top 14 and lower portion 30 of the container body 12 may be formed integrally as a single piece.

The dispenser 10 can be fabricated from acrylonitrile butadiene styrene (ABS), high density polyethylene (HDPE), or other suitable polymeric material. The dispenser 10 may also be fabricated from other materials such as nylon or metal. Manufacturing of the dispenser 10 can be accomplished by injection molding, extruding, stamping, and/or other suitable process depending on the material used. In some embodiments, the dispenser material may be substantially clear or opaque, allowing the user to view the contents within the interior chamber 26 of the dispenser 10.

The top 14 may include a flip-top lid 34, which when opened, exposes an opening through which one or more unused lancets 28 can be removed from within the interior chamber 26. In the illustrative embodiment depicted, the flip-top lid 34 may be hingedly connected to a portion of the top 14 via a hinge 36. In those embodiments where the dispenser 10 is fabricated from a polymeric material, for example, the lid 34 may be hingedly connected to the top 14 via a living hinge. Other means for hingedly connecting the lid 34 to the top 14 may be employed such as, for example, a friction hinge, lift-off hinge, or butt hinge. A small notch 38 adjacent to a pivoting end 40 of the lid 34 can be provided to facilitate lifting of the lid 34 with the user's fingers.

In some embodiments, and as further shown in FIG. 1, the top 14 of the dispenser 10 may further include a gripping element which, as is discussed in greater detail below with respect to FIG. 5, can be used to facilitate removal of the protective caps 58 from the lancets 28. The gripping element may include an indentation 42 inset a short distance below a top surface 44 on the exterior of the container body 12, and can have an elliptical and, in some cases, circular shape that conforms generally to the size and shape of the protective cap. The size and shape of the indentation 42 may vary, however, depending on the configuration of the protective cap 58 or other portion of the medical instrument being removed. The indentation 42 may be located adjacent to the side 22 opposite the free end 40 of the lid 34, or can be located elsewhere on the container body 12, if desired.

Figure 2:
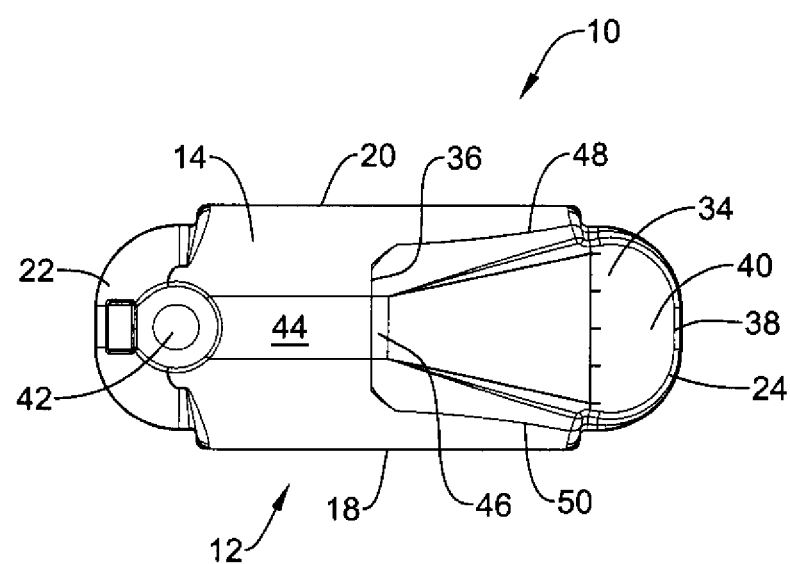
FIG. 2 is a top view of the medical dispenser of FIG. 1.
Figure 3:
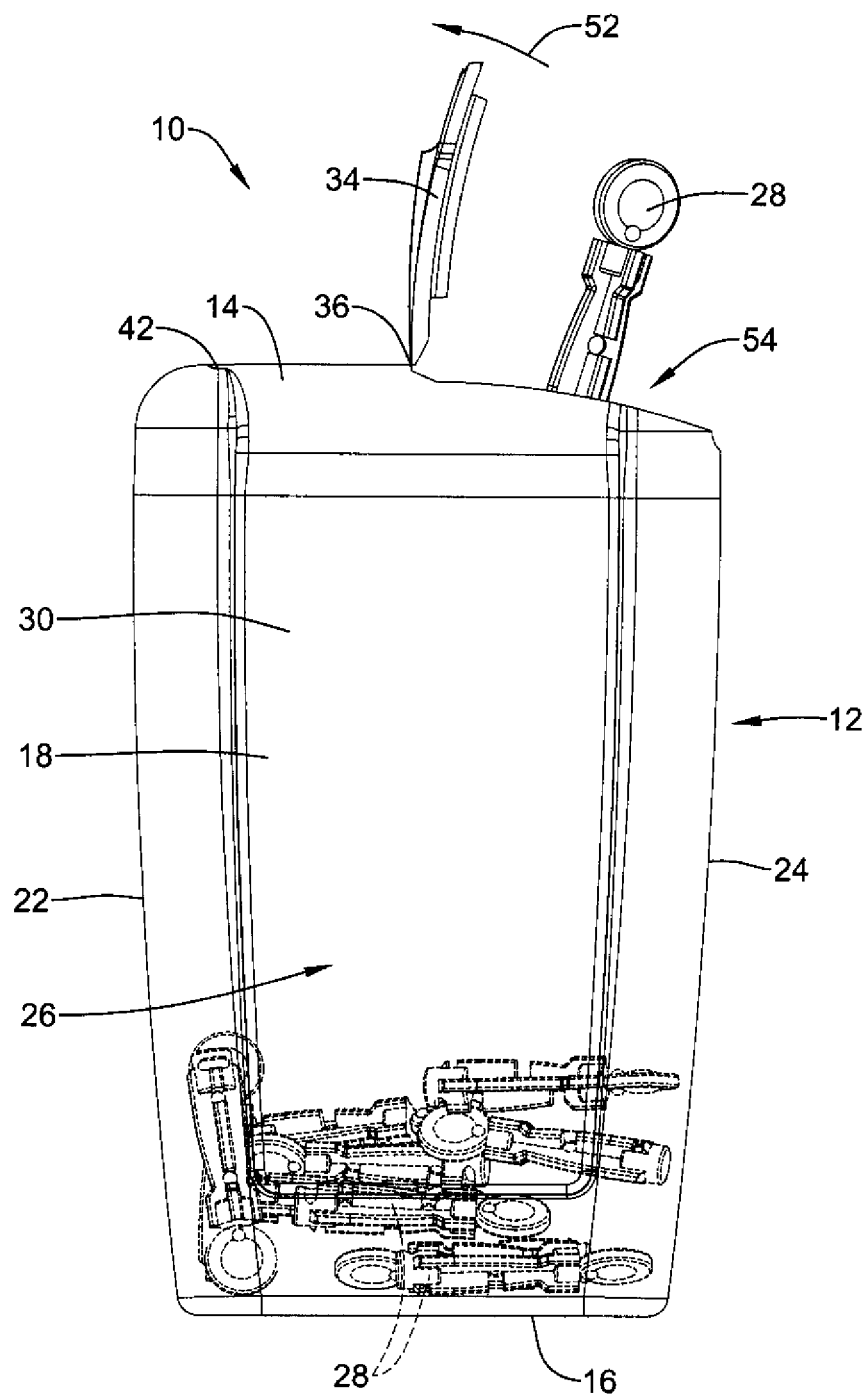
FIG. 3 is a side view showing the removal of a lancet from the medical dispenser of FIG. 1.

FIG. 2 is a top view of the medical dispenser 10 of FIG. 1. As can be further seen in FIG. 2, the lid 34 may have a fixed end 46, a number of sides 48,50, and an unconstrained, pivoting end 40 opposite the fixed end 46. In the illustrative embodiment depicted, the lid 34 may have an elongated shape with the sides 48,50 having a length greater than the length of the ends 40,46. In use, the lid 34 may be opened by inserting the user's finger into the notch 38 and then prying the lid 34 upwardly. As further shown in FIG. 3, this causes the lid 34 to pivot about the hinge 36 and open in the direction indicated generally by arrow 52, exposing an opening 54 within the top 14 that can be used to remove a lancet 28 or other medical instrument from within the interior chamber 26. Removal of a lancet 28 may occur, for example, by tilting the dispenser 10 upside down and then shaking the container body 12 until a lancet 28 is released through the opening 54. The opening 54 can be sized and shaped to permit only a single lancet 28 from being removed from the dispenser 10 at a time, or alternatively, can be configured to permit multiple lancets 28 to be removed at once.

Figure 4:
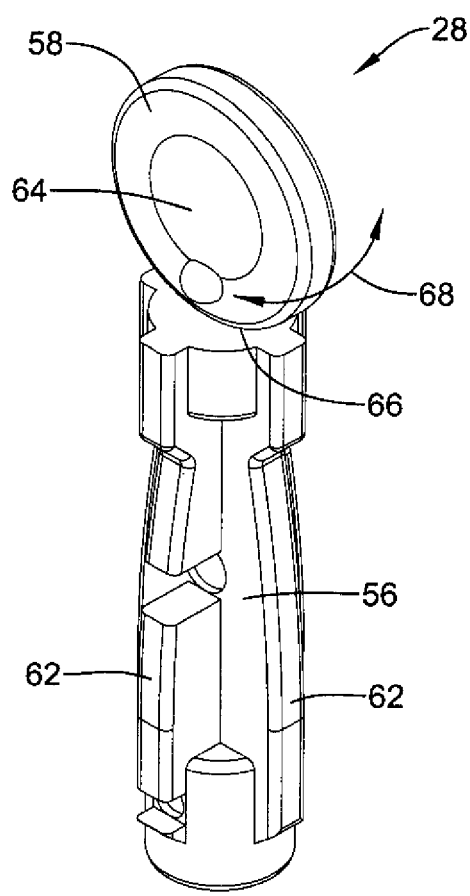
FIG. 4 is a perspective view of a lancet.
Figure 5:
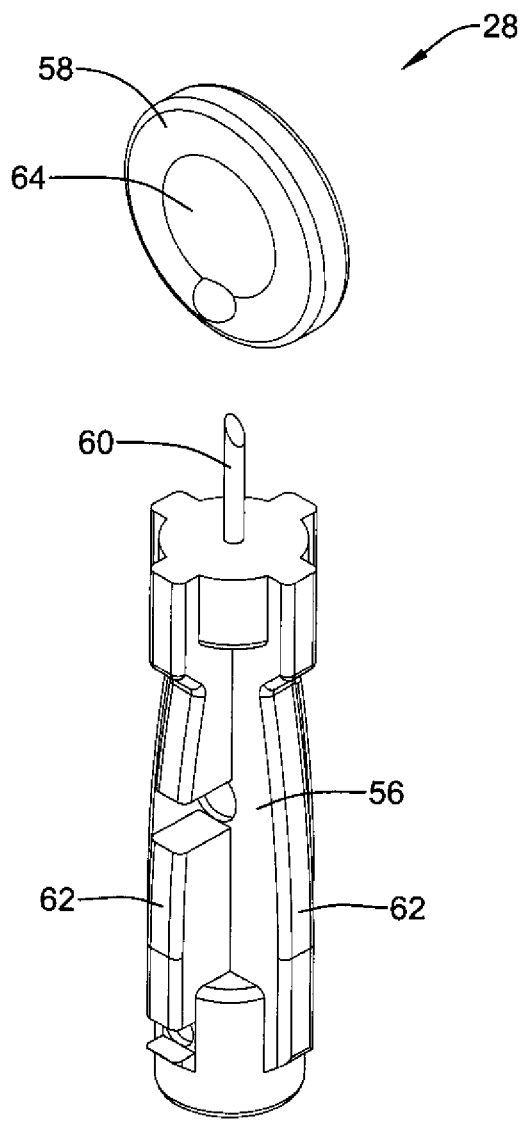
FIG. 5 is a perspective view showing the protective cap removed from the lancet of FIG. 4.

FIG. 4-5 are perspective views showing an illustrative lancet 28 that can be stored within the dispenser 10 of FIG. 1. As shown in FIGS. 4-5, the lancet 28 may have a handle grip 56 for gripping the lancet 28 and a protective cap 58 that can be used to cover and maintain the sterility of the sharp needle tip 60. The handle grip 56 may include a number of ribs 62 to facilitate gripping of the handle grip 56. The cap 58, in turn, may have a bulbous shaped formed by a number of outwardly extending dimples 64 on each side of the cap 58, which may also facilitate gripping of the cap 58.

Prior to use, and as shown in FIG. 4, the protective cap 58 can be removably attached to the handle grip 56 at a tear joint 66. Typically, removal of the protective cap 58 is accomplished manually gripping the handle grip 56 with the user's fingers, and then twisting the protective cap 58 in either a clockwise or counterclockwise direction, as indicated generally by arrow 66 in FIG. 4. The twisting of the protective cap 58 in this manner causes the cap 58 to pivot about the joint 62, causing the cap 58 to tear off from the handle grip 56. As shown in FIG. 5, the removal of the protective cap 58 from the lancet 28 exposes the needle tip 60 for use. The lancet 28 can then be used to obtain a blood sample by pricking the needle tip 60 into the user's finger, earlobe, or other anatomy and then collecting the blood sample on a test strip or the like. In some cases, the lancet 28 can be loaded into a lancing device for collecting a blood sample, if desired.

The removal of the protective cap 58 from the lancet 28 may be difficult for certain users depending on the user's dexterity and strength. For example, the relatively small size of the handle grip 56 provided on many commercially available lancets 28 may make it difficult for the user to adequately grip the protective cap 28 as it is removed from the handle grip 56.

Figure 6:
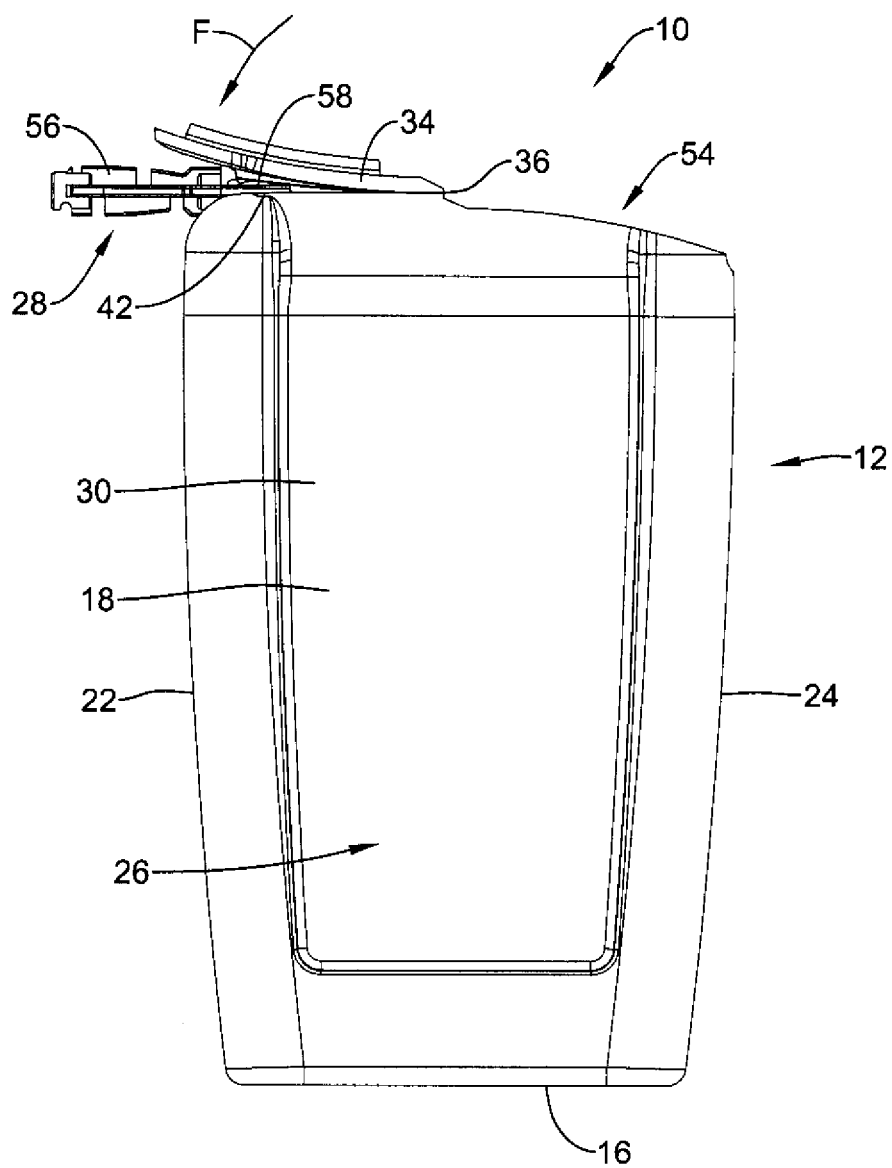
FIG. 6 is a perspective view showing the lancet of FIG. 4 inserted into the indentation on the medical dispenser.
Figure 7:
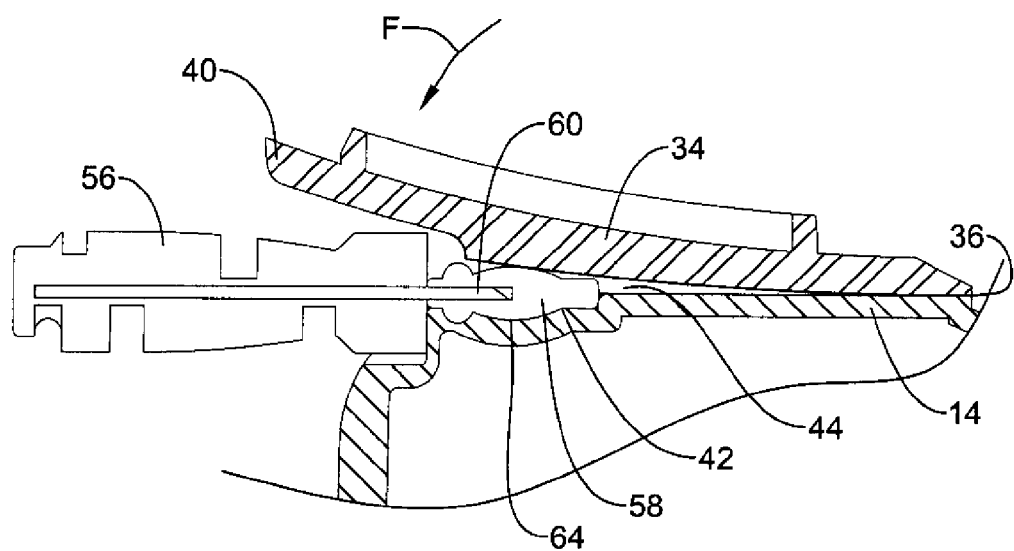
FIG. 7 is a cross-sectional view showing the lancet of FIG. 6 restrained within the indentation.

To facilitate removal of the protective cap 58, the user may insert the cap 58 into the indentation 42 on the top 14 of the container body 12, and then open the lid 34 fully. As illustrated in FIG. 6, for example, when the protective cap 58 is inserted into the indentation 42 and the lid 34 is in a fully open position, the lid 34 can be configured to restrain the cap 58 within the indentation 42, thereby preventing its removal. The user may hold the protective cap 58 in place within the indentation 42 by applying a downwardly directed force to the lid 34 in the direction indicated generally by arrow F. In this position, and as shown further in a cross-sectional view in FIG. 7, the cap 58 is restrained within the indentation 42 due to the bulbous shape of the dimples 64 and the downwardly directed force F of the lid 34, which applies friction to the cap 58. Once restrained within the indentation 42 in this manner, the handle grip 56 can then be rotated while holding the dispenser 10 stationary, or alternatively rotating the dispenser 10 while holding the handle grip 56 stationary, causing the handle grip 56 to tear-away from the protective cap 58. The protective cap 58 can then be removed from within the indentation 42 and either discarded or saved for future use.

Figure 8:
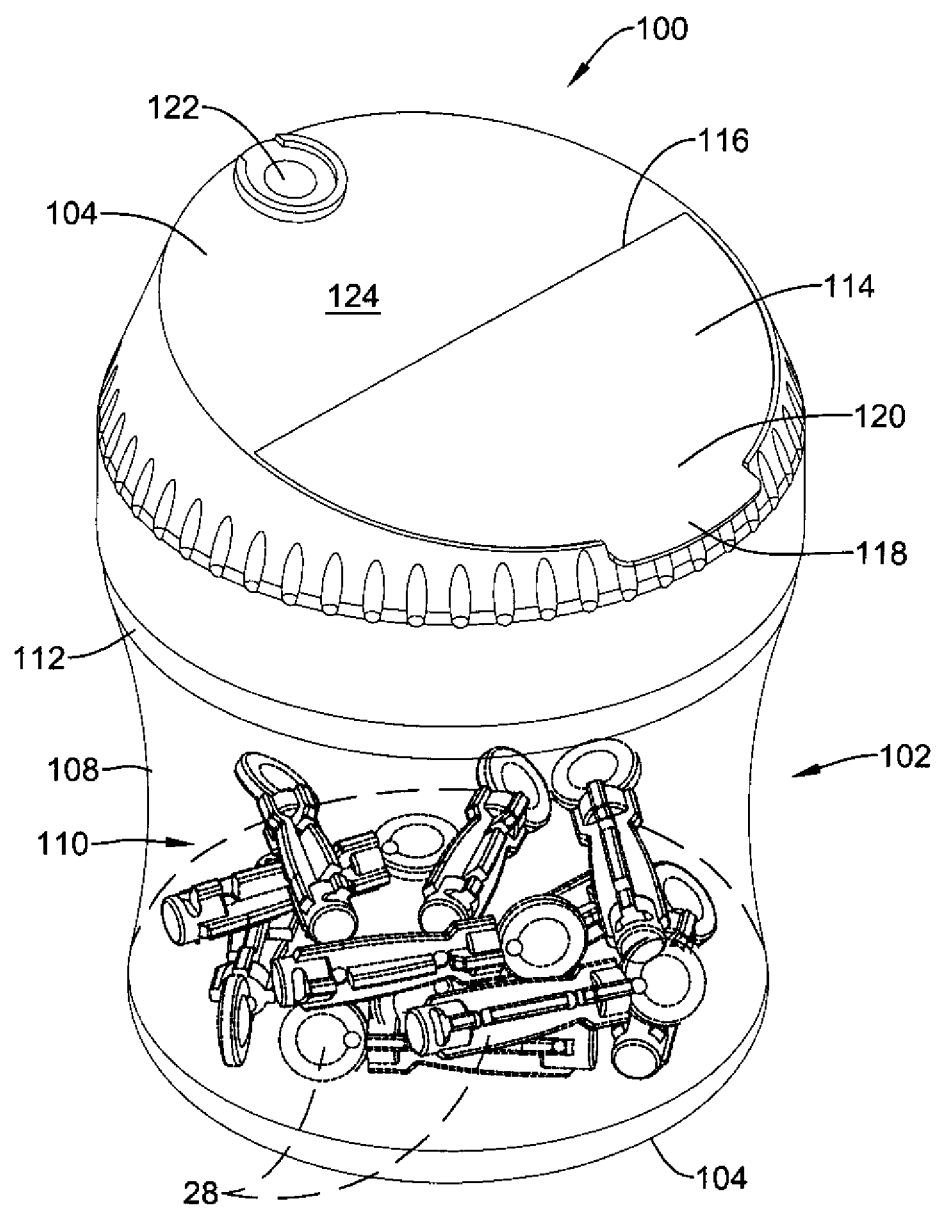
FIG. 8 is a perspective view showing a medical dispenser in accordance with another illustrative embodiment.

FIG. 8 is a perspective view of a medical dispenser 100 in accordance with another illustrative embodiment. The medical dispenser 100 may be similar to that described above with respect to FIG. 1, including a container body 102 having top 104, a bottom 106, and a sidewall 108, which together define a container structure having an interior chamber 110 adapted to store a number of unused lancets, sharps, or other medical instruments therein. As shown in phantom, for example, the interior chamber 110 may contain a number of unused lancets 28 that can be used to obtain a blood sample from the user. In the illustrative embodiment depicted, the dispenser 100 has a substantially cylindrical shape, although other configurations are possible.

The dispenser 100 can be configured to function as either a disposable dispenser, or alternatively, as a reusable dispenser that can be reloaded with lancets 28 or other medical instruments. In some embodiments, the top 104 can be made removable from the sidewall 108 via a seam 112, allowing the user to refill the interior chamber 110 by removing the top 104. Alternatively, and in other embodiments, the top 104 can be fixedly secured to or formed integrally with the sidewall 108 to prevent the top 104 from being removed by the user.

The top 104 may include a flip-top lid 114 which, when opened, exposes an opening 134 through which one or more lancets 28 can be removed from within the interior chamber 110. The flip-top lid 112 may be hingedly connected to a portion of the top 104 via a hinge 116 such as a living hinge, friction hinge, lift-off hinge, butt hinge, etc. A tab 118 extending from the free end 120 of the lid 114 can be provided to facilitate lifting of the lid 114 with the user's fingers.

The top 104 of the dispenser 100 may further include a gripping element such as an indentation 122 that can be used to facilitate removal of the protective caps 58 from the lancets 28. The indentation 122 may be formed on the top surface 124 of the container body 102, and can have an elliptical and, in some cases, circular shape that conforms generally to the size and shape of the protective cap 58. The configuration of the indentation 122, including its size, shape and/or location on the container body 12 may vary from that depicted, however.

Figure 9:
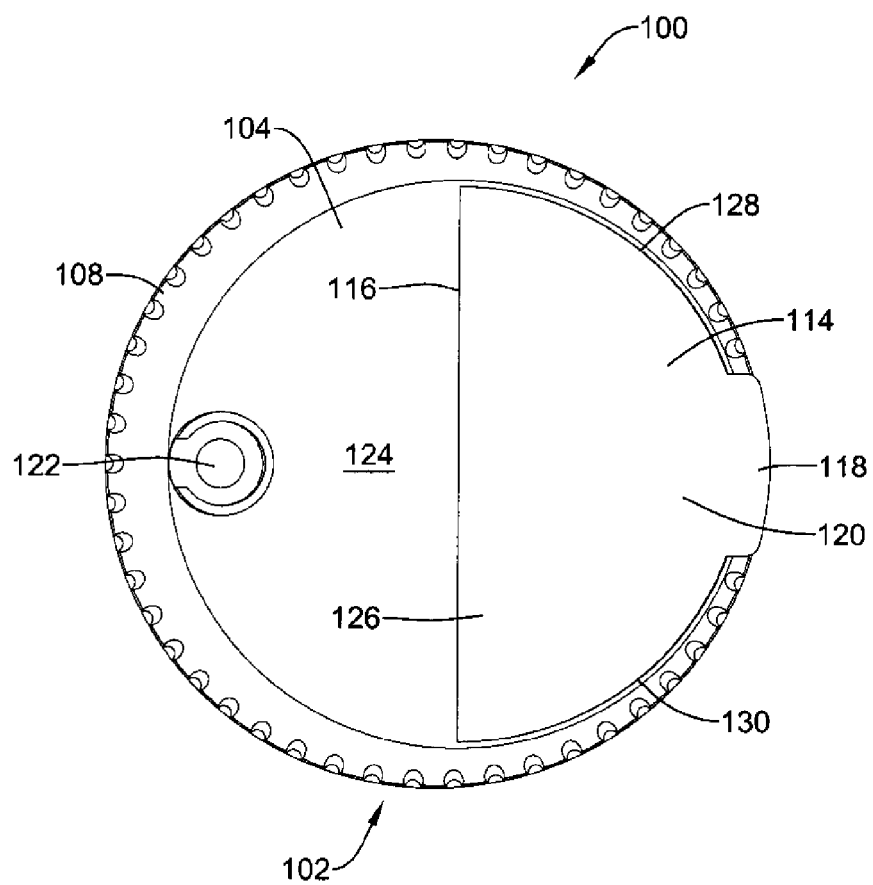
FIG. 9 is a top view of the medical dispenser of FIG. 8.
Figure 10:
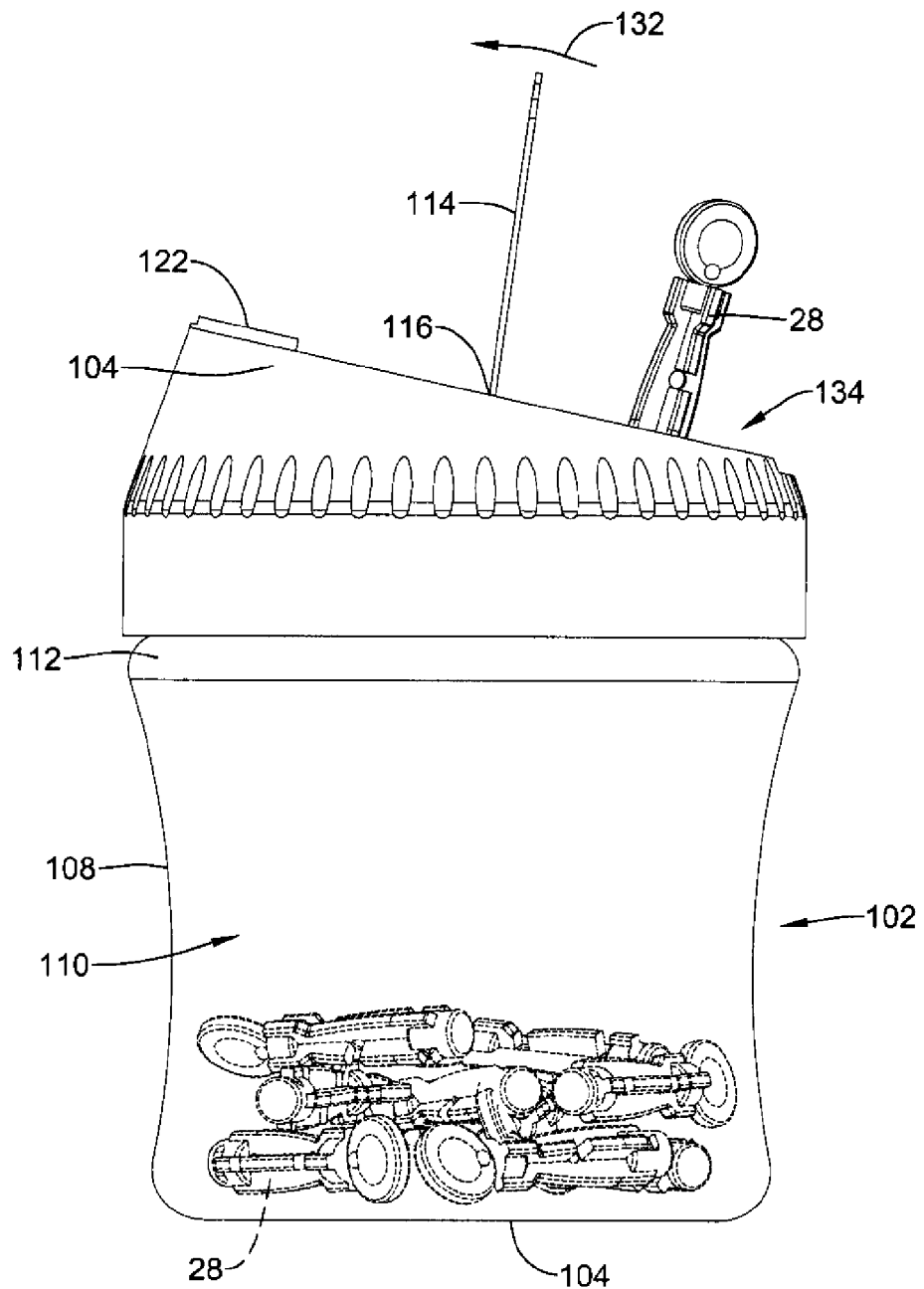
FIG. 10 is a side view showing the removal of a lancet from the medical dispenser of FIG. 8.

FIG. 9 is a top view of the medical dispenser 100 of FIG. 1. As can be further seen in FIG. 9, the lid 114 may have a fixed end 126, a number of sides 128,130, and an unconstrained, pivoting end 120 opposite the fixed end 126. In the illustrative embodiment depicted, the lid 114 may have a semi-circular shape, although other configurations are possible. In use, the lid 114 may be opened by grasping the tab 118 and then prying the lid 114 open. As further shown in FIG. 10, this causes the lid 114 to pivot about the hinge 116 and open in the direction indicated generally by arrow 132, exposing an opening 134 within the top 104 that can be used to remove one or more lancets 28 or other medical instruments from within the interior chamber 110. Removal of a lancet 28 may occur, for example, by tilting the dispenser 100 upside down and then shaking the container body 102 until a lancet 28 is released through the opening 134. The opening 134 can be sized and shaped to permit only a single lancet 28 from being removed from the dispenser 100 at a time, or alternatively, can be configured to permit multiple lancets 28 to be removed at once.

Figure 11:
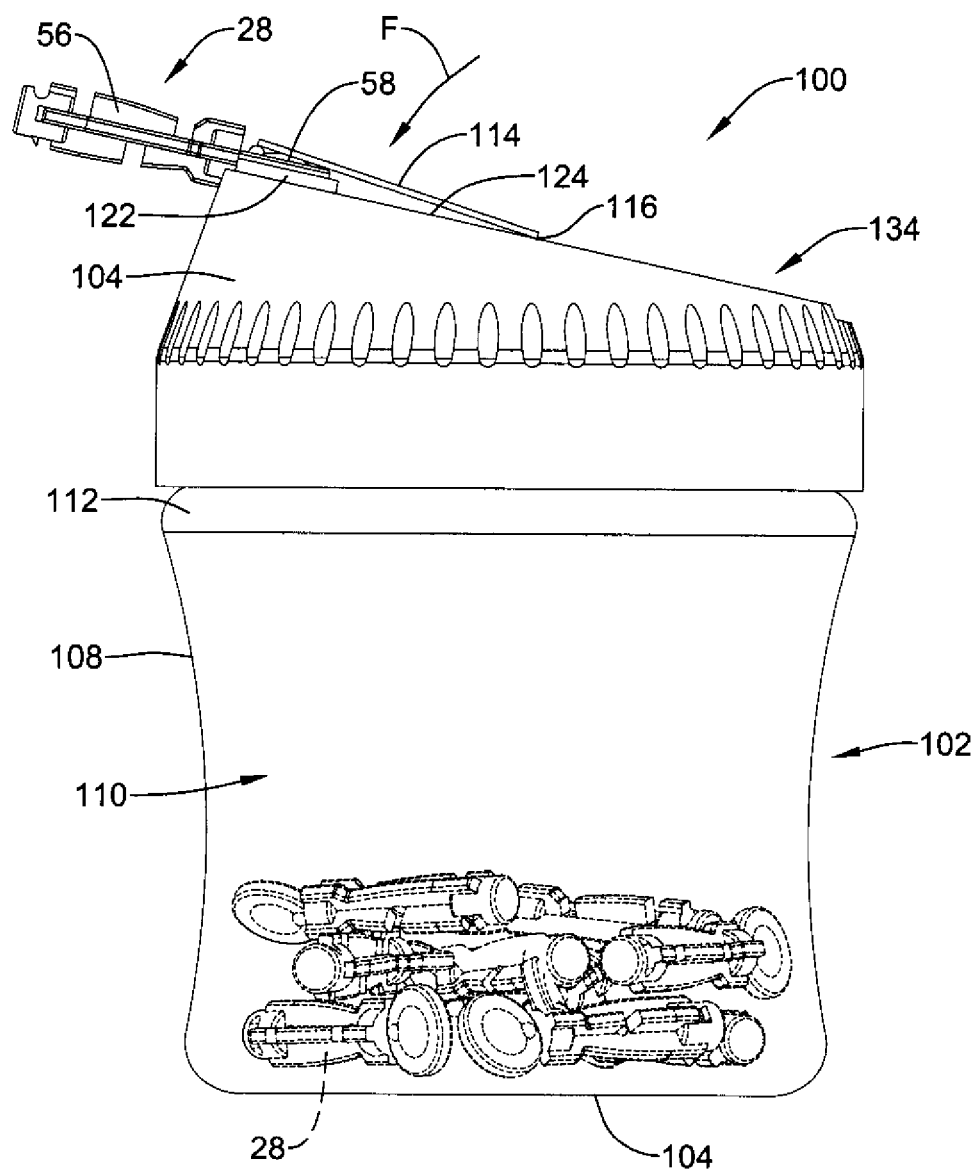
FIG. 11 is a perspective view showing the insertion of a lancet into the indentation.
Figure 12:
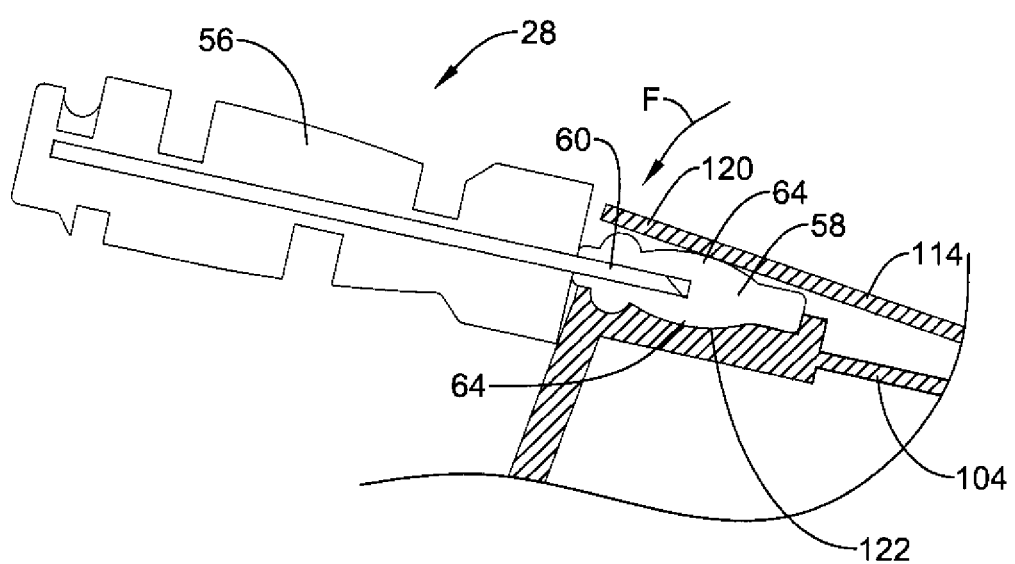
FIG. 12 is a cross-sectional view showing the lancet inserted into the indentation.

FIG. 11 is a perspective view showing the insertion of a lancet 28 into the indentation 122. As illustrated in FIG. 11, when the protective cap 58 is inserted into the indentation 122 and the lid 114 is fully opened, the lid 114 can be configured to restrain the cap 58 within the indentation 122 thereby preventing its removal. The user may then hold the protective cap 58 in place by applying a downwardly directed force F to the lid 114. As further shown in cross-sectional view in FIG. 12, the cap 58 is restrained within the indentation 122 due to the bulbous shape of the dimples 64 and the downwardly directed force F of the lid 114, which applies friction to the cap 58. In this position, the cap 58 can then be removed from the handle grip 56 and then removed from within the indentation 122 and either discarded or saved for future use.

As can be further seen in FIG. 11, the top surface 124 of the container body 102 may be sloped at an angle, orienting the indentation 122 at an angle slightly offset from horizontal. In use, this offset orientation of the indentation 122 acts to orient the lancet handle grip 56 at a slight vertical angle when inserted into the indentation 122 in order to facilitate gripping of the handle grip 56 by the user's fingers as the protective cap 58 is being removed.

Figure 13:
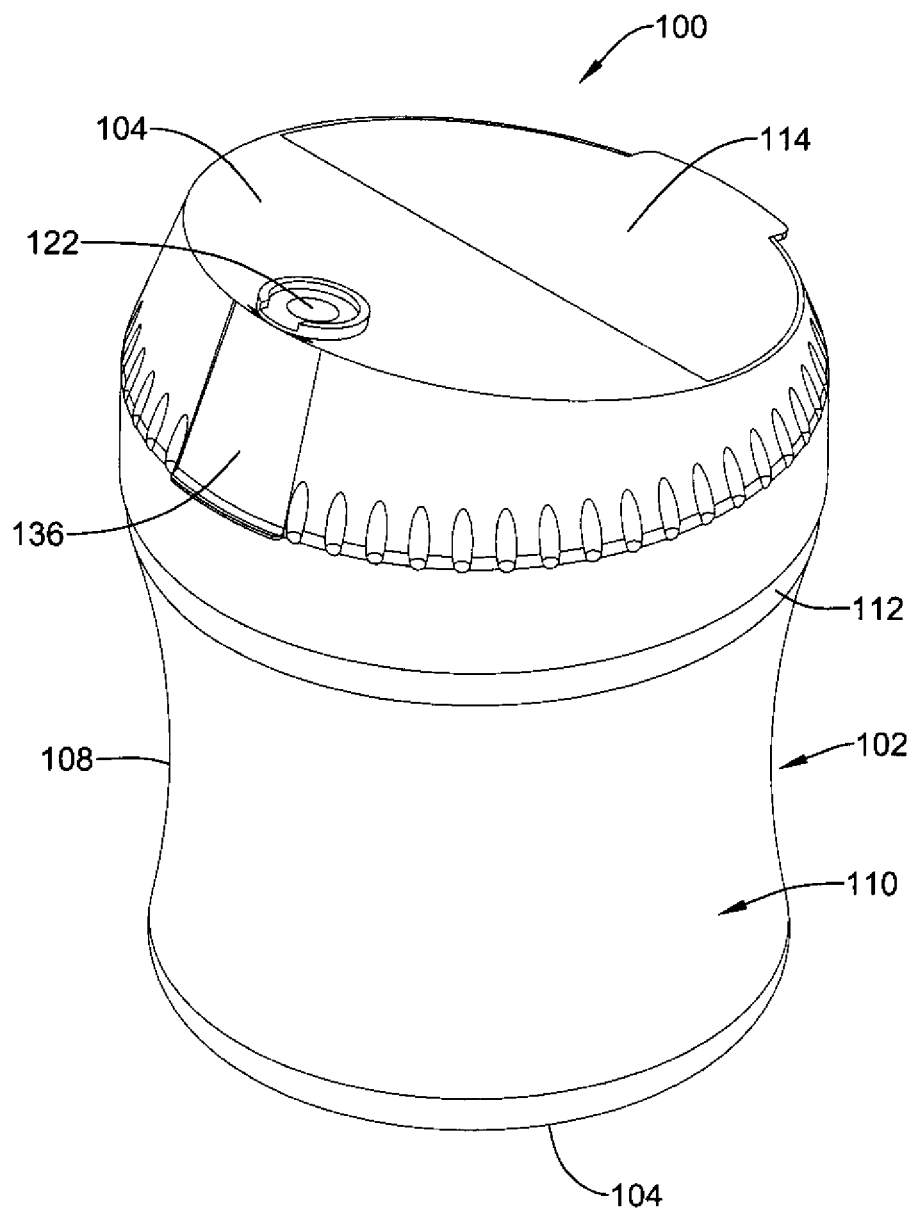
FIG. 13 is a perspective view showing a medical dispenser in accordance with another illustrative embodiment having multiple lids.

Although the medical dispensers 10,100 each include a single lid that can be used to access the contents within the interior chamber, it should be understood that the dispenser can be further equipped with one or more additional lids, if desired. In one alternative embodiment depicted in FIG. 13, for example, the medical dispenser 100 may be equipped with a second lid 136 that can also be opened to gain access to the contents within the interior chamber 110. The second lid 136 may be smaller than the first lid 114, allowing each of the lids 114,136 to function differently. For example, the relatively large lid 114 may be used to refill the dispenser 100 with unused lancets or to dispense multiple lancets 28 at a time whereas the relatively small lid 136 may be used to serially dispense lancets 28 one at a time. Other configurations are possible, however.

Figure 14:
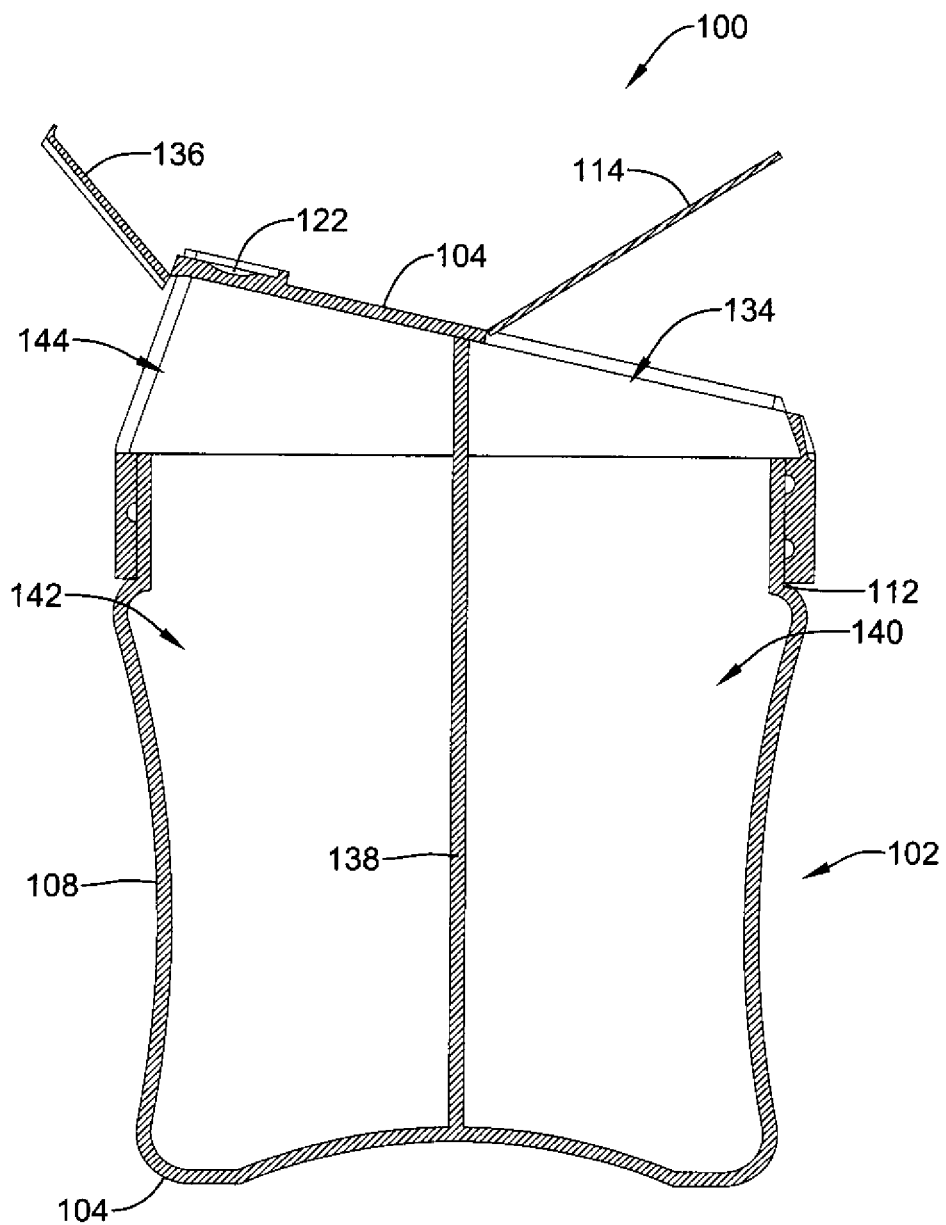
FIG. 14 is a side cross-sectional view showing the medical dispenser of FIG. 13 equipped with an interior partition or dividing wall.

In some embodiments, the medical dispenser 10,100 can also be configured to receive used lancets or other such medical instruments, if desired. In one alternative embodiment depicted in FIG. 14, for example, the container body 102 can include an interior partition or dividing wall 138 that separates a first interior chamber 140 of the dispenser 100 from a second interior chamber 142 thereof. The first interior chamber 138 can be configured to store one or more unused medical devices (e.g. lancets) whereas the second interior chamber 140 can be configured to receive used medical waste. The first and second interior chambers 138,140 can be isolated from each other to maintain the sterility of the unused lancets 28 within the first chamber 138. Access to the first interior chamber 138 can be accomplished via the first lid 114, which can be opened to expose a first opening 134 on the top 104 to gain access to the unused lancets. Access to the second interior chamber 140 can be accomplished, in turn, via the second lid 136, which can be opened to expose a second opening 144 on the top 104 for receiving used lancets.

Having thus described the several embodiments of the present invention, those of skill in the art will readily appreciate that other embodiments may be made and used which fall within the scope of the claims attached hereto. It will be understood that this disclosure is, in many respects, only illustrative. Changes can be made with respect to various elements described herein without exceeding the scope of the invention.

What is claimed is:

1. A medical dispenser, comprising:
 a container body having a top, a bottom, and a number of sidewalls defining an interior chamber adapted to contain one or more unused medical instruments therein;
 at least one opening mechanism on the container body comprising a lid actuatable between a first position and a second position for opening or closing one or more openings on the container body, the one or more openings being sized and adapted to permit the disbursement of one or more unused medical instruments within the interior chamber; and
 a gripping element adapted to receive a portion of a medical instrument inserted therein, wherein said gripping element includes an indentation on an exterior portion of the container body configured to receive a portion of the unused medical instrument;

wherein the lid associated with the at least one opening mechanism is adapted to pivot towards and frictionally engage a portion of the unused medical instrument when the unused medical instrument is inserted into the indentation and when the opening mechanism is in the first position.

2. The medical dispenser of claim 1, wherein the at least one opening mechanism includes a lid hingedly connected to the top of the container body.

3. The medical dispenser of claim 2, wherein the lid is hingedly connected to the container body via a living hinge.

4. The medical dispenser of claim 1, wherein the at least one opening includes a first opening and a second opening.

5. The medical dispenser of claim 4, wherein the second opening is larger than the first opening.

6. The medical dispenser of claim 4, wherein the container body further includes a partition or dividing wall forming a first interior chamber and second interior chamber.

7. The medical dispenser of claim 6, wherein the first interior chamber is configured to contain a number of unused medical instruments whereas the second interior chamber is configured to receive a number of used medical instruments.

8. The medical dispenser of claim 1, wherein the container body is formed from a substantially clear or opaque material.

9. The medical dispenser of claim 1, wherein the one or more unused medical instruments includes one or more lancets each having a handle grip and a removable cap.

10. The medical dispenser of claim 9, wherein the gripping element includes an indentation on an exterior portion of the container body configured to receive the removable cap from an unused lancet.

11. The medical dispenser of claim 10, wherein the indentation is inset within a top surface of the container body.

12. The medical dispenser of claim 11, wherein the top surface of the container body is sloped.

13. A lancet dispenser for dispensing lancets having a handle grip removably coupled to a protective cap, the lancet dispenser comprising:

a container body having a top, a bottom, and a number of sidewalls defining an interior chamber adapted to contain one or more lancets therein;

at least one opening mechanism on the container body comprising a lid actuatable between a first position and a second position for opening or closing one or more openings on the container body, the one or more openings being sized and adapted to permit the disbursement of one or more unused lancets within the interior chamber; and a gripping element on the exterior of the container body, the gripping element including an indentation on the container body adapted to receive therein a portion of the protective cap from an unused lancet;

wherein the lid associated with the at least one opening is adapted to pivot towards and frictionally engage a portion of the protective cap when inserted into the indentation and when the opening mechanism is in the first position.

14. The lancet dispenser of claim 13, wherein the at least one opening mechanism includes a lid hingedly connected to the top of the container body.

15. The lancet dispenser of claim 14, wherein the lid is hingedly connected to the container body via a living hinge.

16. The lancet dispenser of claim 13, wherein the at least one opening includes a first opening and a second opening.

17. The lancet dispenser of claim 16, wherein the second opening is larger than the first opening.

18. The lancet dispenser of claim 16, wherein the container body further includes a partition or dividing wall forming a first interior chamber and second interior chamber.

19. The lancet dispenser of claim 18, wherein the first interior chamber is configured to contain a number of unused medical instruments whereas the second interior chamber is configured to receive a number of used medical instruments.

20. The lancet dispenser of claim 13, wherein the container body is formed from a substantially clear or opaque material.

21. The lancet dispenser of claim 13, wherein the indentation is inset within a top surface of the container body.

22. The lancet dispenser of claim 21, wherein the top surface of the container body is sloped.

* * * * *